US011395671B2

(12) United States Patent
Kraemer et al.

(10) Patent No.: US 11,395,671 B2
(45) Date of Patent: **\*Jul. 26, 2022**

(54) FLEXIBLE TRANSORAL ENDOSCOPIC GASTROESOPHAGEAL FLAP VALVE RESTORATION DEVICE AND METHOD

(71) Applicant: EndoGastric Solutions, Inc., Redmond, WA (US)

(72) Inventors: Stefan J. M. Kraemer, Seattle, WA (US); Steve G. Baker, Redmond, WA (US); Brett J. Carter, Moroe, WA (US); John M. Adams, Sammamish, WA (US); John C. Bayne, Redmond, WA (US)

(73) Assignee: EndoGastric Solutions, Inc., Redmond, WA (US)

( * ) Notice: Subject to any disclaimer, the term of this patent is extended or adjusted under 35 U.S.C. 154(b) by 190 days.

This patent is subject to a terminal disclaimer.

(21) Appl. No.: 16/381,302

(22) Filed: Apr. 11, 2019

(65) Prior Publication Data

US 2019/0231375 A1 Aug. 1, 2019

Related U.S. Application Data

(60) Division of application No. 15/389,741, filed on Dec. 23, 2016, now Pat. No. 10,299,814, which is a division of application No. 12/873,233, filed on Aug. 31, 2010, now Pat. No. 9,526,500, which is a continuation of application No. 11/893,549, filed on
(Continued)

(51) Int. Cl.
*A61B 17/29* (2006.01)
*A61B 17/00* (2006.01)
*A61B 17/064* (2006.01)
*A61B 17/068* (2006.01)
*A61B 17/10* (2006.01)

(52) U.S. Cl.
CPC ........ *A61B 17/29* (2013.01); *A61B 17/00234* (2013.01); *A61B 17/068* (2013.01); *A61B 17/0643* (2013.01); *A61B 17/10* (2013.01); *A61B 2017/003* (2013.01); *A61B 2017/00827* (2013.01); *A61B 2017/2905* (2013.01)

(58) Field of Classification Search
CPC .............. A61B 17/068; A61B 17/0643; A61B 2017/00827; A61B 2017/00314; A61B 2017/2908; A61B 2017/2947; A61B 2017/2927; A61B 2017/00818
See application file for complete search history.

(56) References Cited

U.S. PATENT DOCUMENTS 5,143,475 A * 9/1992 Chikama .............. A61B 1/0051
  248/160
5,152,744 A * 10/1992 Krause ............. A61B 17/32002
  604/22

(Continued)

*Primary Examiner* — Alexander J Orkin
(74) *Attorney, Agent, or Firm* — Fulwider Patton LLP

(57) ABSTRACT

A transoral gastroesophageal flap valve restoration device has sufficient flexibility and dimension to be passed through the mouth, throat, and esophagus of a patient into the patient's stomach. The device includes a first member and a second member hingedly coupled to the first member. The first and second members are configured to flex in a direction to follow the esophageal path into the stomach and to be substantially rigid when forming the restored gastroesophageal flap valve.

11 Claims, 6 Drawing Sheets

Related U.S. Application Data

Aug. 15, 2007, now abandoned, which is a continuation of application No. 11/001,666, filed on Nov. 30, 2004, now abandoned.

(56) References Cited

U.S. PATENT DOCUMENTS

| | | | | |
|---|---|---|---|---|
| 5,381,782 | A * | 1/1995 | DeLaRama | A61B 1/0056 |
| | | | | 138/118 |
| 5,454,787 | A * | 10/1995 | Lundquist | A61B 10/0233 |
| | | | | 604/95.01 |
| 5,558,665 | A * | 9/1996 | Kieturakis | A61B 17/0218 |
| | | | | 600/139 |
| 5,759,151 | A * | 6/1998 | Sturges | A61B 1/00078 |
| | | | | 600/139 |
| 6,086,600 | A * | 7/2000 | Kortenbach | A61B 1/00087 |
| | | | | 606/139 |
| 9,526,500 | B2 * | 12/2016 | Carter | A61B 17/0643 |
| 10,299,814 | B2 * | 5/2019 | Kraemer | A61B 17/29 |
| 2001/0056282 | A1 * | 12/2001 | Sonnenschein | A61B 1/00181 |
| | | | | 606/139 |
| 2002/0082585 | A1 * | 6/2002 | Carroll | A61M 25/0141 |
| | | | | 604/528 |
| 2002/0082621 | A1 * | 6/2002 | Schurr | A61B 17/0643 |
| | | | | 606/151 |
| 2005/0222601 | A1 * | 10/2005 | Erhard | A61B 17/0218 |
| | | | | 606/190 |
| 2006/0106288 | A1 * | 5/2006 | Roth | A61B 17/0218 |
| | | | | 600/204 |

* cited by examiner

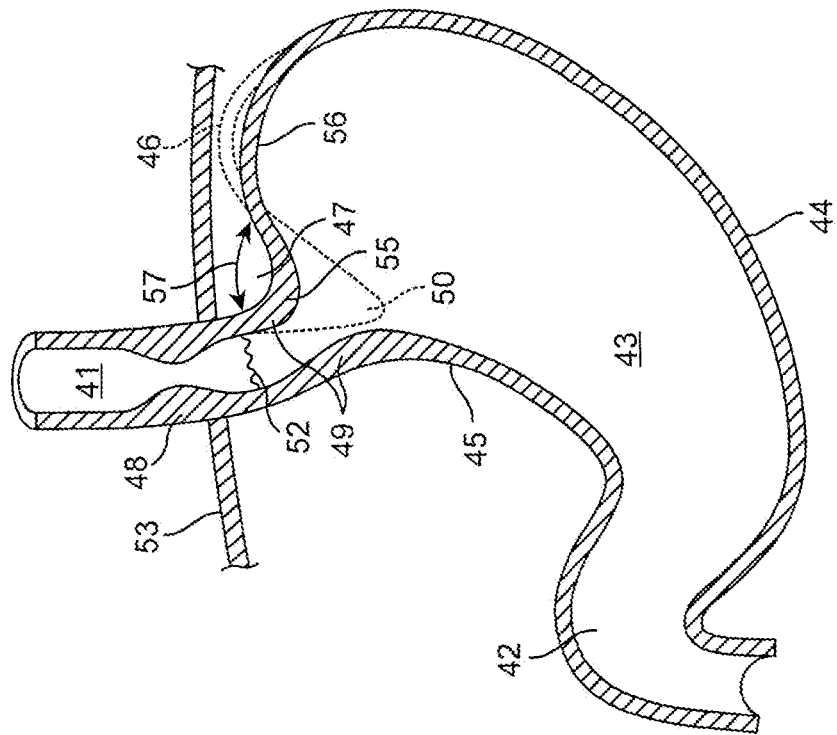
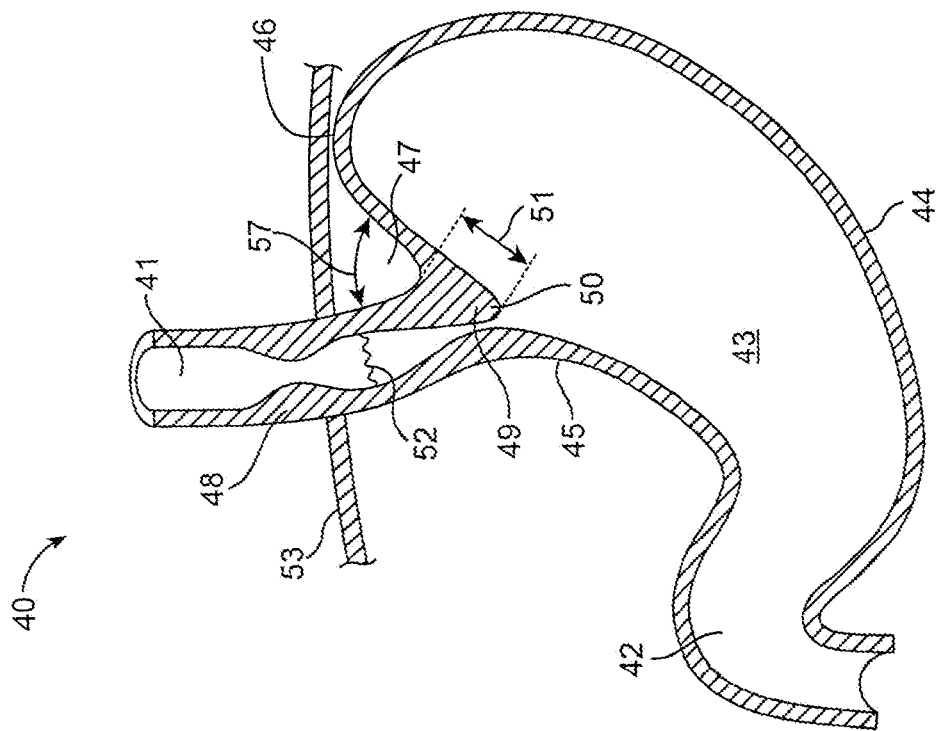
FIG. 1
FIG. 2

FLEXIBLE TRANSORAL ENDOSCOPIC GASTROESOPHAGEAL FLAP VALVE RESTORATION DEVICE AND METHOD

This Preliminary Amendment is being filed concurrently with an application that is a division of Ser. No. 15/389,741 filed Dec. 23, 2016, which is a division of Ser. No. 12/873,233 filed Aug. 31, 2010, now U.S. Pat. No. 9,526,500 issued Dec. 27, 2016, which is a continuation of Ser. No. 11/893,549 filed Aug. 15, 2007, now abandoned, which is a continuation of Ser. No. 11/001,666 filed Nov. 30, 2004, now abandoned, the entirety of each of which are incorporated herein by reference.

FIELD OF THE INVENTION

The present invention generally relates to devices for treating gastroesophageal reflux disease. The present invention more particularly relates to such devices which are flexible enough for passage into the stomach while being capable of being made selectively rigid for forming a gastroesophageal flap.

BACKGROUND

Gastroesophageal reflux disease (GERD) is a chronic condition caused by the failure of the anti-reflux barrier located at the gastroesophageal junction to keep the contents of the stomach from splashing into the esophagus. The splashing is known as gastroesophageal reflux. The stomach acid is designed to digest meat, and will digest esophageal tissue when persistently splashed into the esophagus.

A principal reason for regurgitation associated with GERD is the mechanical failure of a deteriorated gastroesophageal flap to close and seal against high pressure in the stomach. Due to reasons including lifestyle, a Grade I normal gastroesophageal flap may deteriorate into a malfunctioning Grade III or absent valve Grade IV gastroesophageal flap. With a deteriorated gastroesophageal flap, the stomach contents are more likely to be regurgitated into the esophagus, the mouth, and even the lungs. The regurgitation is referred to as "heartburn" because the most common symptom is a burning discomfort in the chest under the breastbone. Burning discomfort in the chest and regurgitation (burping up) of sour-tasting gastric juice into the mouth are classic symptoms of gastroesophageal reflux disease (GERD). When stomach acid is regurgitated into the esophagus, it is usually cleared quickly by esophageal contractions. Heartburn (backwashing of stomach acid and bile onto the esophagus) results when stomach acid is frequently regurgitated into the esophagus and the esophageal wall is inflamed.

Complications develop for some people who have GERD. Esophagitis (inflammation of the esophagus) with erosions and ulcerations (breaks in the lining of the esophagus) can occur from repeated and prolonged acid exposure. If these breaks are deep, bleeding or scarring of the esophagus with formation of a stricture (narrowing of the esophagus) can occur. If the esophagus narrows significantly, then food sticks in the esophagus and the symptom is known as dysphagia. GERD has been shown to be one of the most important risk factors for the development of esophageal adenocarcinoma. In a subset of people who have severe GERD, if acid exposure continues, the injured squamous lining is replaced by a precancerous lining (called Barrett's Esophagus) in which a cancerous esophageal adenocarcinoma can develop.

Other complications of GERD may not appear to be related to esophageal disease at all. Some people with GERD may develop recurrent pneumonia (lung infection), asthma (wheezing), or a chronic cough from acid backing up into the esophagus and all the way up through the upper esophageal sphincter into the lungs. In many instances, this occurs at night, while the person is in a supine position and sleeping. Occasionally, a person with severe GERD will be awakened from sleep with a choking sensation. Hoarseness can also occur due to acid reaching the vocal cords, causing a chronic inflammation or injury.

GERD never improves without intervention. Life style changes combined with both medical and surgical treatments exist for GERD. Medical therapies include antacids and proton pump inhibitors. However, the medical therapies only mask the reflux. Patients still get reflux and perhaps emphysema because of particles refluxed into the lungs. Barrett's esophagus results in about 10% of the GERD cases. The esophageal epithelium changes into tissue that tends to become cancerous from repeated acid washing despite the medication.

Several open laparotomy and laproscopic surgical procedures are available for treating GERD. One surgical approach is the Nissen fundoplication. The Nissen approach typically involves a 360° wrap of the fundus around the gastroesophageal junction. The procedure has a high incidence of postoperative complications. The Nissen approach creates a 360° moveable flap without a fixed portion. Hence, Nissen does not restore the normal movable flap. The patient cannot burp because the fundus was used to make the repair, and may frequently experience dysphagia. Another surgical approach to treating GERD is the Belsey Mark IV (Belsey) fundoplication. The Belsey procedure involves creating a valve by suturing a portion of the stomach to an anterior surface of the esophagus. It reduces some of the postoperative complications encountered with the Nissen fundoplication, but still does not restore the normal movable flap. None of these procedures fully restores the normal anatomical anatomy or produces a normally functioning gastroesophageal junction. Another surgical approach is the Hill repair. In the Hill repair, the gastroesophageal junction is anchored to the posterior abdominal areas, and a 180° valve is created by a system of sutures. The Hill procedure restores the moveable flap, the cardiac notch and the Angle of His. However, all of these surgical procedures are very invasive, regardless of whether done as a laproscopic or an open procedure.

New, less surgically invasive approaches to treating GERD involve transoral endoscopic procedures. One procedure contemplates a machine device with robotic arms that is inserted transorally into the stomach. While observing through an endoscope, an endoscopist guides the machine within the stomach to engage a portion of the fundus with a corkscrew-like device on one arm. The arm then pulls on the engaged portion to create a fold of tissue or radial plication at the gastroesophageal junction. Another arm of the machine pinches the excess tissue together and fastens the excess tissue with one pre-tied implant. This procedure does not restore normal anatomy. The fold created does not have anything in common with a valve. In fact, the direction of the radial fold prevents the fold or plication from acting as a flap of a valve.

Another transoral procedure contemplates making a fold of fundus tissue near the deteriorated gastroesophageal flap to recreate the lower esophageal sphincter (LES). The procedure requires placing multiple U-shaped tissue clips around the folded fundus to hold it in shape and in place.

This and the previously discussed procedure are both highly dependent on the skill, experience, aggressiveness, and courage of the endoscopist. In addition, these and other procedures may involve esophageal tissue in the repair. Esophageal tissue is fragile and weak. Involvement of esophageal tissue in the repair of a gastroesophageal flap valve poses unnecessary risks to the patient.

A new and improved device and method for restoration of a gastroesophageal flap valve is fully disclosed in U.S. Pat. No. 6,790,214, issued Sep. 14, 2004, for TRANSORAL ENDOSCOPIC GASTROESOPHAGEAL FLAP VALVE RESTORATION DEVICE, ASSEMBLY, SYSTEM AND METHOD, which patent is assigned to the assignee of this invention, and is incorporated herein by reference. That apparatus and method provides transoral endoscopic gastroesophageal flap valve restoration. A longitudinal member arranged for transoral placement into a stomach carries a tissue shaper that non-invasively grips and shapes stomach tissue. A tissue fixation device is then deployed to maintain the shaped stomach tissue in a shape approximating a gastroesophageal flap.

Whenever stomach tissue is to be transorally shaped as, for example, by the improved device last mentioned above, it is necessary to feed the device down the esophageal passage including the mouth, throat, and esophagus and into the stomach. Unfortunately, the throat and esophagus are capable of expanding to only a diameter of about two centimeters (2 cm) without damage. Further, the back of throat defines a radius of approximately only 4.4 cm in the average adult. Hence, for any kind of device to be guided down into the stomach, the device must have a maximum perimeter of no more than about 6.28 cm (2 cm×π) and be flexible enough to bend through the radius of 4.4 cm defined by the back of the throat. While being flexible enough to travel down the throat and esophagus, the device must also be rigid enough to shape the stomach tissue necessary to form the gastroesophageal flap. The present invention addresses these issues.

SUMMARY

The invention provides a transoral gastroesophageal flap valve restoration device comprising a first member, and a second member hingedly coupled to the first member. The first and second members are arranged for esophageal passage into a stomach to receive stomach tissue there between and to form a flap of a gastroesophageal flap valve. The first and second members are configured to flex in a direction to follow the esophageal path into the stomach and to be substantially rigid when receiving the stomach tissue there between to form the flap of the gastroesophageal flap valve.

The invention further provides an assembly for restoring a gastroesophageal flap valve comprising a longitudinal member having an end arranged for placement in a stomach, and a transoral gastroesophageal flap valve restoration device carried at the end of the longitudinal member including a first member and a second member hingedly coupled to the first member. The first and second members are arranged for esophageal passage into a stomach to receive stomach tissue there between and to form a flap of a gastroesophageal flap valve. The first and second members are also configured to flex in a direction to follow the esophageal path into the stomach but to also be substantially rigid when receiving the stomach tissue there between and forming the flap of the gastroesophageal flap valve.

According to another embodiment, the invention provides a transoral gastroesophageal flap valve restoration device that is selectively flexible during mouth, throat, and esophagus passage into a stomach, and selectively comparatively rigid during folding of stomach tissue into a restored gastroesophageal flap.

The invention further provides a method of restoring a gastroesophageal flap valve. The method comprises providing a transoral gastroesophageal flap valve restoration device comprising a first member and a second member hingedly coupled to the first member, the first and second members being flexible for esophageal passage into a stomach and substantially rigid to receive stomach tissue there between to form a flap of a gastroesophageal flap valve when in a second orientation. The method further comprises feeding the device down the esophagus into the stomach with the device in a flexible condition, rendering the device substantially rigid, and pulling stomach tissue between the first and second members to form the flap of the gastroesophageal flap valve.

The invention still further provides a method of restoring a gastroesophageal flap valve comprising the steps of providing a transoral gastroesophageal flap valve restoration device arranged for esophageal passage into a stomach when in a substantially flexible condition and to receive stomach tissue to form a flap of a gastroesophageal flap valve when in a substantially rigid condition. The method further comprises feeding the device down the esophagus into the stomach with the device in the substantially flexible condition, rendering the device into the substantially rigid condition, and pulling stomach tissue into the device to form the flap of the gastroesophageal flap valve.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawings, in the several figures of which like referenced numerals identify like elements, and wherein:

FIG. 1 is a front cross-sectional view of the esophageal-gastro-intestinal tract from a lower portion of the esophagus to the duodenum;

FIG. 2 is a front cross-sectional view of the esophageal-gastro-intestinal tract illustrating a Grade I normal appearance movable flap of the gastroesophageal flap valve (in dashed lines) and a Grade III reflux appearance gastroesophageal flap of the gastroesophageal flap valve (in solid lines);

DETAILED DESCRIPTION

Figure 4:
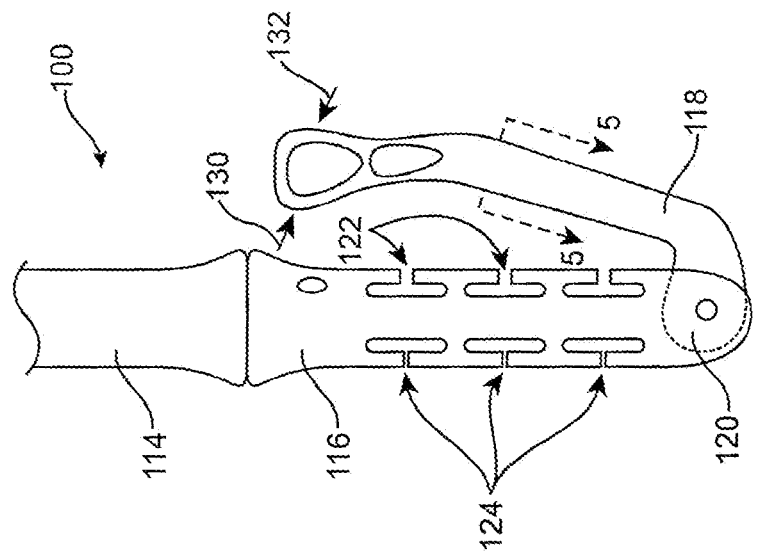
FIG. 4 is a side view of the device of FIG. 3.

FIG. 1 is a front cross-sectional view of the esophageal-gastro-intestinal tract 40 from a lower portion of the esophagus 41 to the duodenum 42. The stomach 43 is characterized by the greater curvature 44 on the anatomical left side and the lesser curvature 45 on the anatomical right side. The tissue of the outer surfaces of those curvatures is referred to in the art as serosa tissue. As will be seen subsequently, the nature of the serosa tissue is used to advantage for its ability to bond to like serosa tissue. The fundus 46 of the greater curvature 44 forms the superior portion of the stomach 43, and traps gas and air bubbles for burping. The esophageal tract 41 enters the stomach 43 at an esophageal orifice below the superior portion of the fundus 46, forming a cardiac notch 47 and an acute angle with respect to the fundus 46 known as the Angle of His 57. The lower esophageal sphincter (LES) 48 is a discriminating sphincter able to distinguish between burping gas, liquids, and solids, and works in conjunction with the fundus 46 to burp. The gastroesophageal flap valve (GEFV) 49 includes a moveable portion and an opposing more stationary portion. The moveable portion of the GEFV 49 is an approximately 180°, semicircular, gastroesophageal flap 50 (alternatively referred to as a "normal moveable flap" or "moveable flap") formed of tissue at the intersection between the esophagus 41 and the stomach 43. The opposing more stationary portion of the GEFV 49 comprises a portion of the lesser curvature 45 of the stomach 43 adjacent to its junction with the esophagus 41. The gastroesophageal flap 50 of the GEFV 49 principally comprises tissue adjacent to the fundus 46 portion of the stomach 43, is about 4 to 5 cm long (51) at it longest portion, and the length may taper at its anterior and posterior ends. The gastroesophageal flap 50 is partially held against the lesser curvature 45 portion of the stomach 43 by the pressure differential between the stomach 43 and the thorax, and partially by the resiliency and the anatomical structure of the GEFV 49, thus providing the valving function. The GEFV 49 is similar to a flutter valve, with the gastroesophageal flap 50 being flexible and closeable against the other more stationary side.

The esophageal tract is controlled by an upper esophageal sphincter (UES) in the neck near the mouth for swallowing, and by the LES 48 and the GEFV 49 at the stomach. The normal anti-reflux barrier is primarily formed by the LES 48 and the GEFV 49 acting in concert to allow food and liquid to enter the stomach, and to considerably resist reflux of stomach contents into the esophagus 41 past the gastroesophageal tissue junction 52. Tissue aboral of the gastroesophageal tissue junction 52 is generally considered part of the stomach because the tissue protected from stomach acid by its own protective mechanisms. Tissue oral of the gastroesophageal junction 52 is generally considered part of the esophagus and it is not protected from injury by prolonged exposure to stomach acid. At the gastroesophageal junction 52, the juncture of the stomach and esophageal tissues form a zigzag line, which is sometimes referred to as the "Z-line." For the purposes of these specifications, including the claims, "stomach" means the tissue aboral of the gastroesophageal junction 52.

FIG. 2 is a front cross-sectional view of an esophageal-gastro-intestinal tract illustrating a Grade I normal appearance movable flap 50 of the GEFV 49 (shown in dashed lines) and a deteriorated Grade III gastroesophageal flap 55 of the GEFV 49 (shown in solid lines). As previously mentioned, a principal reason for regurgitation associated with GERD is the mechanical failure of the deteriorated (or reflux appearance) gastroesophageal flap 55 of the GEFV 49 to close and seal against the higher pressure in the stomach. Due to reasons including lifestyle, a Grade I normal gastroesophageal flap 50 of the GEFV 49 may deteriorate into a Grade III deteriorated gastroesophageal flap 55. The anatomical results of the deterioration include moving a portion of the esophagus 41 that includes the gastroesophageal junction 52 and LES 48 toward the mouth, straightening of the cardiac notch 47, and increasing the Angle of His 57. This effectively reshapes the anatomy aboral of the gastroesophageal junction 52 and forms a flattened fundus 56. The deteriorated gastroesophageal flap 55 illustrates a gastroesophageal flap valve 49 and cardiac notch 47 that have both significantly degraded. Dr. Hill and colleagues developed a grading system to describe the appearance of the GEFV and the likelihood that a patient will experience chronic acid reflux. L. D. Hill, et al., *The gastroesophageal flap valve: in vitro and in vivo observations*, Gastrointestinal Endoscopy 1996:44:541-547. Under Dr. Hill's grading system, the normal movable flap 50 of the GEFV 49 illustrates a Grade I flap valve that is the least likely to experience reflux. The deteriorated gastroesophageal flap 55 of the GEFV 49 illustrates a Grade III (almost Grade IV) flap valve. A Grade IV flap valve is the most likely to experience reflux. Grades II and III reflect intermediate grades of deterioration and, as in the case of III, a high likelihood of experiencing reflux. With the deteriorated GEFV represented by deteriorated gastroesophageal flap 55 and the fundus 46 moved inferior, the stomach contents are presented a funnel-like opening directing the contents into the esophagus 41 and the greatest likelihood of experiencing reflux. Disclosed subsequently is a device for restoring the normal gastroesophageal flap valve anatomy, which device is one embodiment of the present invention.

Figure 3:
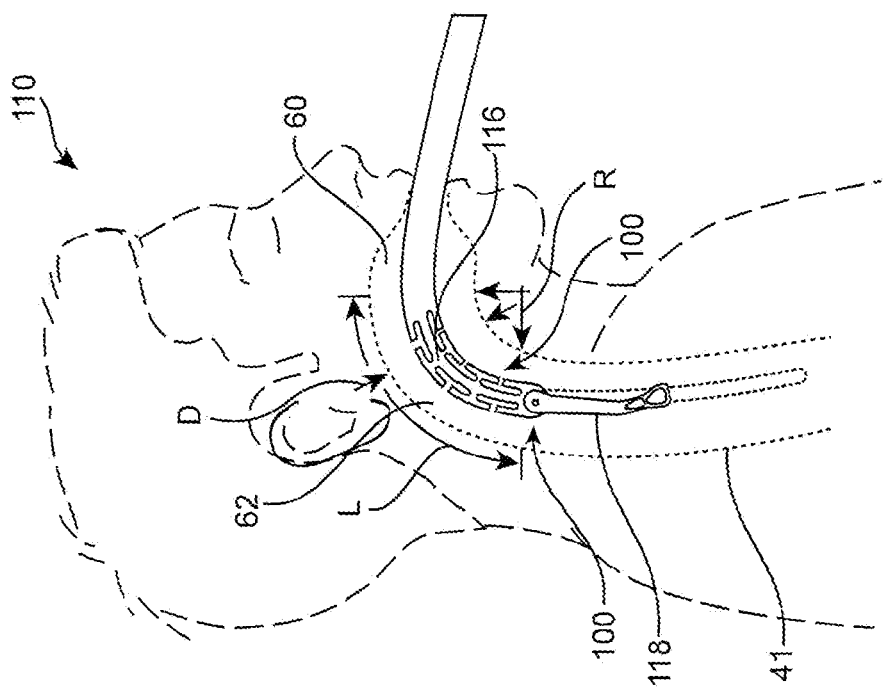
FIG. 3 is a simplified side view of a device according to an embodiment of the invention being fed down an esophageal passage of a patient.

Referring now to FIG. 3, it illustrates a device 100 embodying the present invention being fed through the mouth 60, throat 62, and esophagus 41 of a patient 110. The side view illustrated in FIG. 3 illustrates the obstacles involved in feeding a transoral gastroesophageal flap valve restoration device into the stomach through the esophageal passage including the mouth 60, throat 62, and esophagus 41. As may be noted in FIG. 3, the back of the throat makes a 90° turn in the esophageal passage. The radius of that turn, in most adult patients, will be on the order of 44 mm. The length of the arc of the 90° turn is on the order of 6.75 cm. The diameter of the throat is on the order of 2 cm. The esophageal passageway to the stomach maintains or may be able to maintain a diameter of 2 cm. As a result, a device to be fed through the mouth, and down the throat and esophagus must have a maximum transverse perimeter on the order of 6.28 cm (2 cm×π) or less.

In addition to the restraints on the maximum transverse perimeter, the device must be able to negotiate the 90° turn in the back of the throat. Still further, in order to restore a gastroesophageal flap valve, the flap must be of sufficient length so as to close the esophagus. Hence, the fold is preferably, for example, 3 cm in length or greater. In order to form a fold of 3 cm or greater, a device having a length of 6 cm or greater would be required. Obviously, a rigid device 6 cm in length would have a difficult time in negotiating the 90° turn in the back of the throat.

Accordingly, the gastroesophageal flap valve restoration devices disclosed herein representing various embodiments of the present invention are capable of navigating the 90° turn in the back of the throat without damaging mouth, throat, or esophageal tissue. As will be seen here in each of the embodiments, the devices are dimensioned to follow the esophageal path and configured to flex in a direction to follow the esophageal path while also being configured to be substantially rigid when necessary in forming a restored flap of a gastroesophageal flap valve.

The device 100 according to one embodiment of the present invention is shown in FIG. 4. The device 100 is carried by a longitudinal member 114 which feeds the device 100 down the esophageal passage into the stomach. The device 100 includes a first member or body 116 and a second member or arm 118.

The arm 118 is hingedly coupled to the body 116 by a pulley 120. As a result, the arm 118 is arranged for reciprocal movement with respect to the body 116. When the device 100 is being fed down the esophageal passage, the arm 118 may be rendered to be substantially inline with the body 116 as may be seen in FIG. 3.

To render the body 116 flexible for bending around the 90° turn in the back of the throat as illustrated in FIG. 3, the body 116 includes a plurality of slots comprising a first plurality of slots 122 and a second plurality of slots 124. The first plurality of slots 122 are wider in dimension than the second plurality of slots 124. As a result, the body 116 is capable of bending as illustrated in FIG. 3 for negotiating the 90° turn in the back of the throat.

Figure 5:
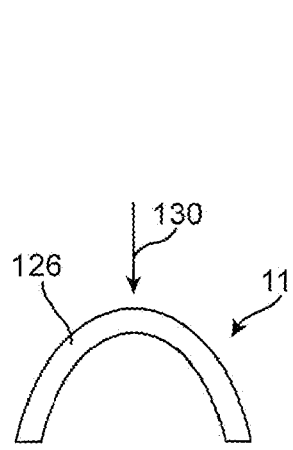
FIG. 5 is a cross-sectional view taken along lines 5-5 of FIG. 4.
Figure 6:
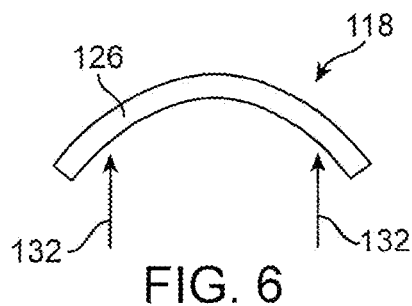
FIG. 6 is a cross-sectional view illustrating the change in the cross-section of FIG. 5 when the device is flexed.

To lend further flexibility to the device 100, the arm 118 is also rendered flexible during the passage down the esophageal passageway. To that end, it will be noted in FIG. 5 that the arm 118 has an arcuate cross-section 126. The concave side of the arm 118 is adjacent the first plurality of slots 122 when the arm 118 is in a substantially closed position as illustrated in FIG. 4. The arcuate cross-section 126 renders the arm 118 substantially rigid with respect to forces applied to the arm 118 in a direction 130 against the concave side of the arcuate configuration 126. However, the arm 118 will be substantially flexible to forces applied in direction 132 substantially opposite that of direction 130. The effect on the arcuate configuration 126 by forces applied in the direction 132 may be seen in FIG. 6. The forces applied in the direction 132 will tend to flex the arm 118 and widen the arcuate configuration 126. Hence, the arm 118 imposes a greater resistance to forces applied in direction 130 than to forces applied in direction 132. Hence, as may be noted in FIG. 3, forces applied to the arm 118 as it negotiates the 90° turn will be in the general direction of the direction 132. As a result, the arm 118 is also capable of flexing for following the esophageal passageway through the throat 62 and down the esophagus 41.

Figure 7:
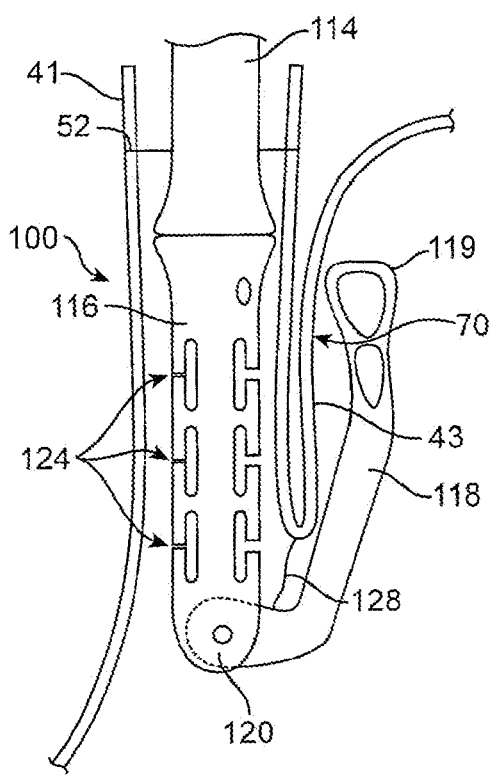
FIG. 7 is a side view of the device of FIG. 3 while restoring a gastroesophageal flap valve according to an embodiment of the invention.

Referring now to FIG. 7, it will be seen that the device 100 has been fed down the esophagus 41 to a position aboral of the gastroesophageal junction or Z-line 52. Stomach tissue 43 has been pulled into the device by a tissue puller 128. Further, the arm 118 has been closed relative to the body 116 to receive the stomach tissue 43 to receive stomach tissue 43 between the body 116 and the arm 118. The body 116 and arm 118 along with the tissue puller 128 creates a fold 70 of stomach tissue 43 aboral of the Z-line 52. Once fasteners (not shown) are driven through the fold 43, the fold is maintained to form a restored gastroesophageal flap valve when the device 100 is removed from the stomach. Suitable fasteners and stomach pullers are described, for example, in co-pending U.S. patent application Ser. No. 10/783,717, filed Feb. 20, 2004, for TISSUE FIXATION DEVICES AND A TRANSORAL ENDOSCOPIC GASTROESOPHAGEAL FLAP VALVE RESTORATION DEVICE AND ASSEMBLY USING SAME, which application is assigned to the assignee of the present invention and incorporated herein in its entirety.

While forming the flap 70 in the stomach tissue 43, the device 100 is rendered substantially rigid. The rigidity of the device is provided by rigidity in both the body 116 and the arm 118. More specifically, because the second set of slots 124 are relatively narrow, they will close when the body 116 is straightened by forces applied to it by the stomach tissue folding process and by a compression assembly to be described hereinafter.

As will also be described hereinafter, the pulley 120 is a single pulley of sufficient diameter to provide a mechanical advantage enclosing arm 118 on the body 116 to enable the stomach tissue 43 to be folded into the flap 70. A pulley of such dimension is rendered possible by a single hinged connection of the arm 118 to the body 116 by the pulley 120. This will be seen more particularly hereinafter.

Figure 8:
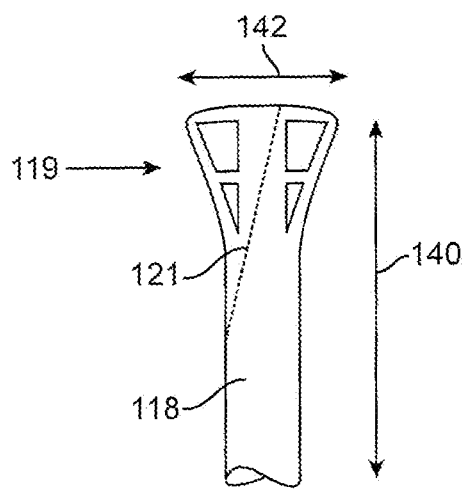
FIG. 8 is a top view of the distal end of the device of FIG. 3.

Referring now to FIG. 8, it is a plan view of the tip end 119 of the arm 118 according to a further embodiment of the present invention. Here, it may be seen that the arm has a longitudinal dimension 140 and a transverse dimension 142. To render the device of further reduced dimension during passage through the esophageal passage, it will be noted in FIG. 8 that the tip end 119 of the arm 118 includes a hinge 121. The hinge 121 may be a living hinge, for example, but other forms of hinge structures may also be employed. The hinge 121 permitted folding of the tip end 119 to reduce the transverse dimension 142 of the tip end 119 of the arm 118.

Figure 9:
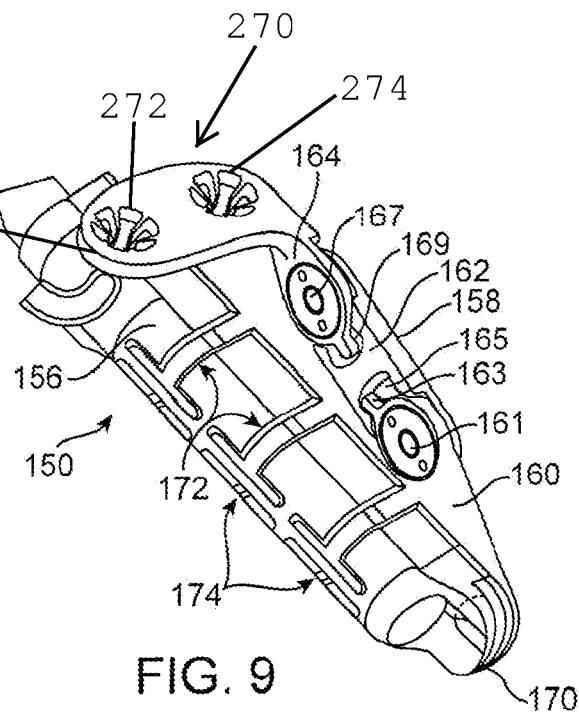
FIG. 9 is a perspective view of another device according to another embodiment of the invention.

Referring now to FIG. 9, it shows another embodiment of the present invention. The device of FIG. 9, denoted by reference character 150, like device 100, includes a body 156 and an arm 158. The arm 158 is hingedly coupled to the body 156 by, for example, a pulley 170. As will be noted in FIG. 9, the body 156 also includes a first plurality of slots 172 and a second plurality of slots 174. The first plurality of slots 172, as in the previous embodiment, are wider then the second plurality of slots 174. The slots 172 and 174 render the body 156 flexible during esophageal passage into the stomach of the device 150 and rigidity of the body 156 during restoration of a gastroesophageal flap valve. The arm 158 is also flexible during esophageal passage of the device 150 but rigid during the formation of a restored gastroesophageal flap valve. To that end, it will be noted that the arm 158 comprises a plurality of links 160, 162, and 164. Link 160 is hingedly coupled to the body 156 at the pulley 170, and is also hingedly coupled to link 162 by a hinge 161. The hinge includes a pin 163 confined within a slot 165 which limits the pivotal movement between link 160 and link 162.

Similarly, link 164 is hingedly coupled to link 162 by another hinge 167. It also includes a pin 169 which limits the pivotal movement between the link 164 and the link 162.

When the device 150 is in the process of forming a restored gastroesophageal flap valve, the links 160, 162, and 164 are locked so as to be substantially inline as shown in FIG. 9. However, when the device 150 is fed down the esophageal passage, the hinges 161, and 167, and the pulley 170, permit the arm 158 to be flexible and conform to the path of the esophageal passage as a device 150 passes through the throat from the mouth to the esophagus. Once the device 150 is within the stomach and forming a flap as generally shown, for example, in FIG. 7, the links 160, 162, and 164 will be locked so as to be rigid for forming the fold in the stomach tissue.

Figure 10:
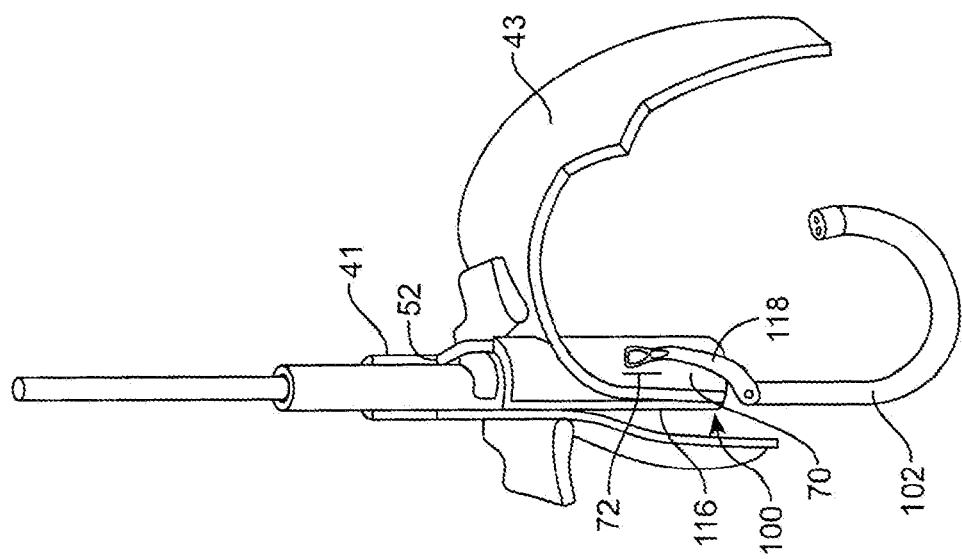
FIG. 10 is a perspective view of the device of FIG. 3 while restoring a gastroesophageal flap valve.

FIG. 10 is a perspective view of the device of FIG. 3 while restoring a gastroesophageal flap valve. Here it may be noted that the flap 70 has been formed by the body 116 and arm 118. A fastener 72 has been deployed to maintain the flap 70.

As will also be noted in FIG. 10, the device 100 permits an endoscope 102 to pass through the body 116 to permit the procedure to be viewed by the medical personnel. As will be seen hereinafter, the device 100 allows the endoscope 102 to be passed there through while maintaining a restricted transverse maximum perimeter to permit the device 100 to be fed down the esophageal passageway into the stomach. As will also be noted in FIG. 10, the fold 70 is being restored aboral of the Z-line 52.

Figure 11:
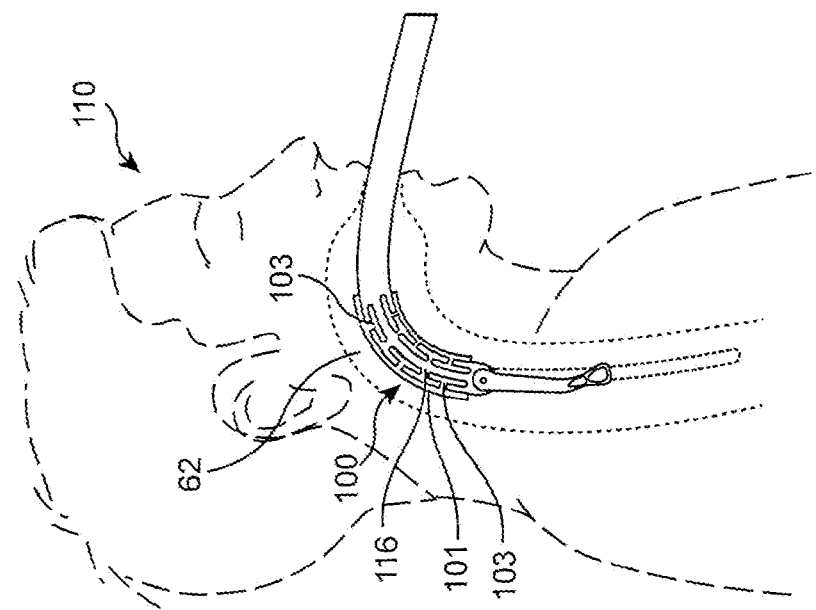
FIG. 11 is a simplified side view of a further embodiment of the invention being fed down an esophageal passage of a patient.

FIG. 11 illustrates another embodiment of the invention. Again, the device 100 is being fed down the back of the throat 62 of the patient 110. The device 100 includes a flexible sheath 101 overlying at least the body 116 of the device 100. The sheath 101 protects the tissue forming the lining of the esophageal passage from any edges which may result from the plurality of slots within the body 116. In addition, or alternatively, the slots may be filled with a flexible filler 103 to present a uniform surface of the body 116 to the tissues lining the esophageal passage. Preferably, the filler material 103 is more flexible than the plastic or other material forming the body 116 and thus has a lower durometer than the material forming the body 116.

Figure 12:
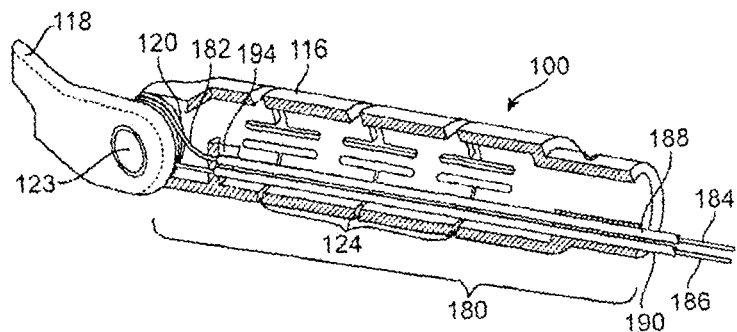
FIG. 12 is a partial perspective side view in cross-section of another device according to an embodiment of the invention.

Referring now to FIG. 12, it is a partial perspective side view of another device 100A illustrating a further embodiment of the present invention. In accordance with this embodiment, the body 116 of the device 100A includes the pulley 120 and a control cable 182. The control cable 182 is at least partially wrapped around the pulley 120 to form a pair of control extensions 184 and 186. The control extensions 184 and 186 are confined within guide tubes 188 and 190 respectively which serve to maintain the cable under tension. It will also be noted that the cable 182 and its control extensions 184 and 186 extend along the longitudinal dimension 192 of the body 116 adjacent to the second and narrower set of slots 124.

When a force 198 is imparted to the control cable 182 to pivot arm 118 pivots for forming the stomach tissue flap. The arm 118 is coupled to the body 116 by a single hinge 123 formed by the pulley 120.

Figure 13:
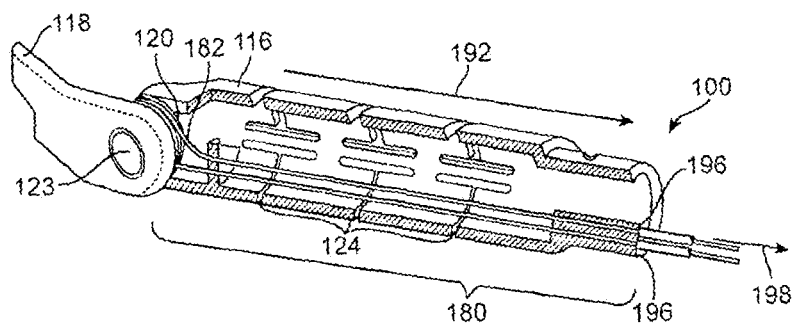
FIG. 13 is another perspective side view in cross-section of another device embodiment of the invention.

Referring now to FIG. 13, it is a partial perspective side view in cross-section of a further device 100A illustrating a further embodiment of the present invention. In accordance with this embodiment, the body 116 of the device 100B includes a compression assembly 180 which selectively renders the body substantially rigid. The compression assembly 180 includes the pulley 120 and the control cable 182. Again, the control cable 182 is at least partially wrapped around the pulley 120 to form a pair of control extensions 184 and 186. The control extensions 184 and 186 are confined within guide tubes 188 and 190 respectively. It will also be noted that the cable 182 and its control extensions 184 and 186 extend along the longitudinal dimension 192 of the body 116 adjacent to the second and narrower set of slots 124. The guide tubes 188 and 190 abut against stop 196.

When the device is fed down the esophageal passageway, the body 116 is flexible and non-compressed. However, when the device 100B is within the stomach aboral of the Z-line and ready to be used for forming a restored gastroesophageal flap valve, the device is rendered substantially rigid. When a force 198 is imparted to the control cable 180 to pivot arm 118 for forming the stomach tissue fold, the body 116 of the device 100 is also placed under compression from the pulley 120 to the stops 196 to ensure closing of the narrow slots 124 and promote rigidity of the body 116 of the device 100B.

As also may be noted in FIG. 13, the arm 118 is coupled to the body 116 by a single hinge 123 thus requiring only a single pulley 120. This single hinge 128 may be more readily seen in FIG. 14.

Figure 14:
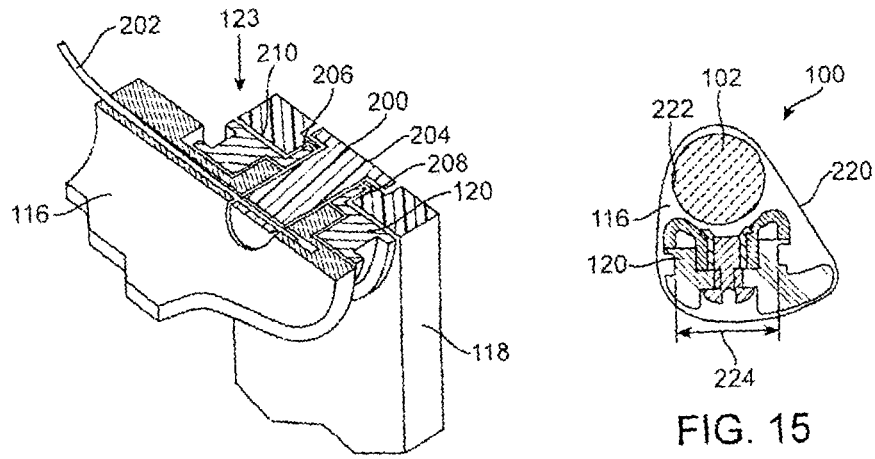
FIG. 14 is a cross-sectional view showing a pulley assembly according to an embodiment of the invention.

As may be seen in FIG. 14, the arm 118, the body 116, and the pulley 120 are held together by a pivot pin 200. The arm 118, pulley 120, and body 116 are held together on the pivot pin 200 by a locking pin 202.

As may be further noted in FIG. 14, the arm 118 includes a slot 204 which is received by flanges 206 and 208 of the pulley 120. The flanges extend substantially parallel to each other across the surface 210 of the pulley 120. The slot 204 of the arm 118 is also received by the pivot pin 200 as shown.

The foregoing structure allows the connection of the arm 118 and the body 116 to be dismantled if necessary. The dismantling of the connection between the arm 118 and the body 116 may be effected by simply pulling the locking pin 220.

Figure 15:
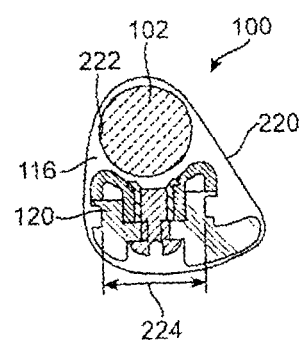
FIG. 15 is a transverse cross-sectional view of a device according to an embodiment of the invention.

Referring now to FIG. 15, it shows a cross-section of the device 100 illustrating its maximum transverse perimeter 220. In FIG. 15, it will be noted that the body 116 includes a passageway 222 to permit the endoscope 102 to pass there through. The passageway 222 may have a diameter of, for example, 11 mm.

Also illustrated in FIG. 15 is the pulley 120. Because only one hinged connection utilized between the arm 118 and body 116, a single pulley is required. Since a single pulley is required, the pulley 120 may have a diameter 224 sufficient to provide a mechanical advantage for imparting reciprocating movement to the arm 118 relative to the body 116 through the pulling of the control cable 182. Hence, even though the device 100 makes provision for an endo scope 102 to be passed there through and a pulley 120 of sufficient diameter to provide a mechanical advantage for operating the arm 118, the device 100 is still able to maintain a maximum perimeter 220 which is no greater than, about, 6.28 cm. Hence, the device has a small enough maximum transverse perimeter to be passed down the esophageal passage including the mouth 60, throat 62, and esophagus 41 (FIG. 3) of a patient.

To provide a sufficient mechanical advantage the pulley 120 may have a diameter greater than about 7 mm. Preferably, the pulley has a diameter of about 10 mm.

Figure 16:
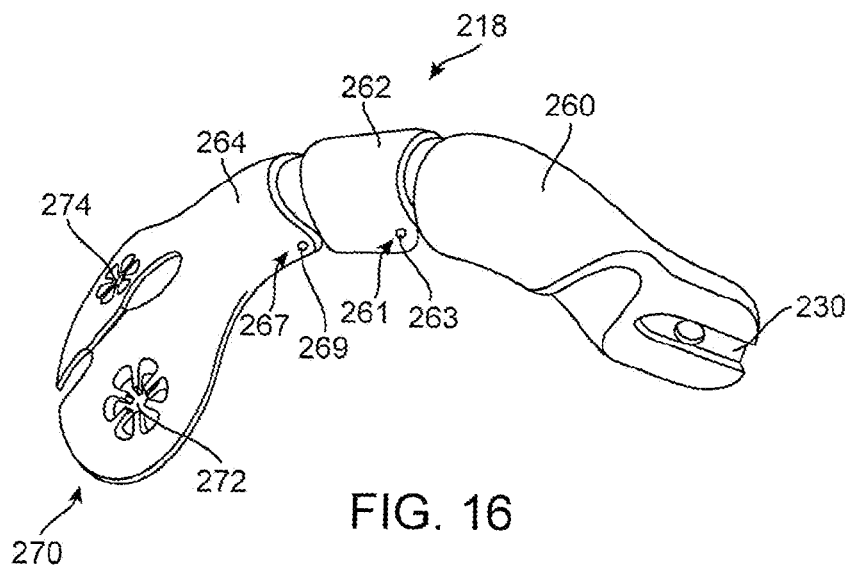
FIG. 16 is a perspective side view of an alternative arm according to a further embodiment of the invention which may be employed in the device of FIGS. 3 and 4 shown in a bent configuration.
Figure 17:
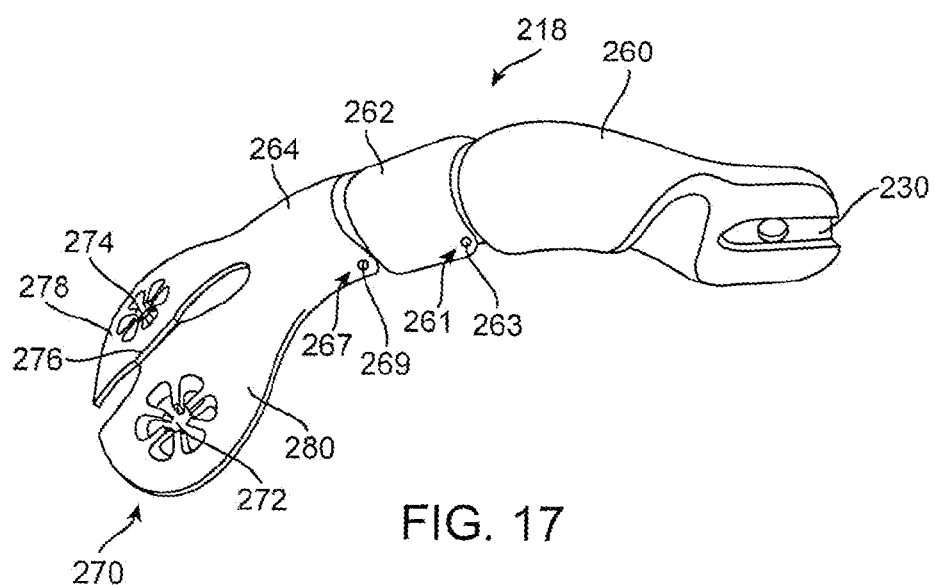
FIG. 17 is a perspective side view of the arm of FIG. 16 shown in a substantially straight configuration.

Referring now to FIGS. 16 and 17, they show another arm 218 according to an embodiment of the present invention which may be employed in the device 100 of FIGS. 3 and 4. The arm 218 may be hingedly coupled to the body 116 by a slot 230 which may slide over the flanges 206 and 208 of the pulley 120 (FIG. 14).

The arm 218 is configured to be flexible during esophageal passage into the stomach of the device 100 and rigid during restoration of a gastroesophageal flap valve. To that end, it will be noted that the arm 218 comprises a plurality of links 260, 262, and 264. Link 260 may be hingedly coupled to the body 116 at the pulley 120, and is also hingedly coupled to link 262 by a hinge 261. The hinge 261 includes a pin 263. Similarly, link 264 is hingedly coupled to link 262 by another hinge 267. It also includes a pin 269.

When the device 100 is fed down the esophageal passage, the hinges 261, and 267, and the pulley 120, permit the arm 218 to be flexible and bent as shown in FIG. 16 to conform to the path of the esophageal passage as the device 100 passes through the throat from the mouth to the esophagus. Once the device 100 is within the stomach and forming a gastroesophageal flap, the links 260, 262, and 264 will be locked to render the arm 218 rigid and substantially straight for forming the fold in the stomach tissue as shown in FIG. 17.

With further reference to FIGS. 16 and 17, it may be noted that the distal end 270 of the arm 218 includes a center slit 276 and is widened to permit broad surface contact with the stomach tissue as the gastroesophageal flap is restored. This widening also accommodates openings 272 and 274. The openings 272 and 274 provide tissue reinforcement as fasteners are driven through the restored gastroesophageal flap in tissue areas defined by the openings 272 and 274.

In view of the widened nature of the distal end 270 of the arm 218, the distal end 270 is preferably comprised of a flexible material which is preformed in a somewhat closed arcuate configuration to reduce the distal end cross-section for passage through the esophageal passage. However, due to the flexible nature of the material used to form the arm 218, and the central slit 276, the wings 278 and 280 formed by the slit 276 will readily fan out and make broad contact with the tissue when the tissue is contacted for forming the gastroesophageal flap.

While particular embodiments of the present invention have been shown and described, modifications may be made, and it is therefore intended in the appended claims to cover all such changes and modifications which fall within the true spirit and scope of the invention.

What is claimed is:

1. A transoral gastroesophageal flap valve restoration device comprising:
    a first member; and
    a second member consisting of a single elongated structure being hingedly coupled to the first member, the first and second members being arranged for esophageal passage into a stomach to receive stomach tissue there between to form a flap of a gastroesophageal flap valve,
    the second member having an arcuate configuration comprising a concave side and a convex side, the second member being substantially rigid with respect to forces applied against the concave side, and the second member being substantially flexible with respect to forces applied in a direction opposite the concave side; and
    the first and second members being configured to flex in a direction to follow an esophageal path into the stomach and to be substantially rigid when receiving the stomach tissue there between and forming the flap of the gastroesophageal flap valve.

2. The device of claim 1 wherein the first member includes a compression assembly that selectively renders the first member substantially rigid.

3. The device of claim 1 wherein each of the first and second members has a length greater than three centimeters.

4. The device of claim 1 wherein each of the first and second members has a length between three and five centimeters.

5. The device of claim 1 wherein the first and second members are arranged to be substantially in line with each other when in the esophageal path.

6. The device of claim 1 wherein the second member has an arcuate cross section.

7. The device of claim 1 wherein one of the first and second members has a longitudinal dimension and wherein the one of the first and second members includes a plurality of slots substantially transverse to the longitudinal dimension of the one of the first and second members.

8. The device of claim 7 further comprising a flexible sheath overlying at least the one of the first and second members.

9. The device of claim 7 further comprising a flexible filler material within the slots.

10. The device of claim 9 wherein the filler material has a lower duro meter than the one of the first and second members.

11. The device of claim 7 wherein the plurality of slots comprises a first set of slots and a second set of slots, the first and second sets of slots being juxtaposed, and the slots of the first set of slots being wider than the slots of the second set of slots.

* * * * *